United States Patent [19]

Richardson et al.

[11] Patent Number: 5,242,602

[45] Date of Patent: Sep. 7, 1993

[54] SPECTROPHOTOMETRIC MONITORING OF MULTIPLE WATER TREATMENT PERFORMANCE INDICATORS USING CHEMOMETRICS

[75] Inventors: John Richardson, Palatine; Larry M. Kye, Hoffman Estates, both of Ill.; Mark D. Brickhouse, Abingdon, Md.; Gary G. Engstrom, Kenosha, Wis.; Kenneth J. Schlager, Elm Grove, Wis.; Scott J. Kahle, Oconomowoc, Wis.; John A. Kelly, Crystal Lake, Ill.

[73] Assignees: W.R. Grace & Co.-Conn., New York, N.Y.; Biotronics Technology, Inc., Waukesha, Wis.

[21] Appl. No.: 845,889

[22] Filed: Mar. 4, 1992

[51] Int. Cl.$^5$ .................... C02F 1/00; G01N 21/31
[52] U.S. Cl. .................... 210/745; 210/143; 356/300; 364/498; 364/500; 436/171
[58] Field of Search ........... 210/85, 94, 95, 96.1, 210/143, 739, 745, 656; 422/82.05, 82.09; 436/171, 39; 364/498, 500, 502; 356/306, 319, 320, 326, 300, 303

[56] References Cited

U.S. PATENT DOCUMENTS

| | | | |
|---|---|---|---|
| 4,783,314 | 11/1988 | Hoots et al. | 210/745 |
| 4,829,533 | 5/1989 | Hallberg et al. | 356/326 |
| 4,966,711 | 10/1990 | Hoots et al. | 210/745 |
| 5,006,311 | 4/1991 | Hoots et al. | 210/745 |
| 5,121,337 | 6/1992 | Brown | 364/498 |
| 5,121,443 | 6/1992 | Tomlinson | 210/656 |
| 5,132,096 | 7/1992 | Hoots et al. | 210/94 |

FOREIGN PATENT DOCUMENTS

| | | | |
|---|---|---|---|
| 320086 | 6/1989 | European Pat. Off. | 210/745 |
| 29073 | 2/1984 | Japan | 210/745 |

OTHER PUBLICATIONS

Article titled "A UV-VIS Spectrophotometer Controlled by a Programmable Desk-Top Calculator", Aaronson et al., vol. 7, No. 9 (Sep. 1975).
Article titled "Simple Derivative Optical Spectrometer", Baldini et al., Applied Optics, vol. 14, No. 11, Nov. 1975 pp. 2687-2690.

Primary Examiner—Joseph W. Drodge
Attorney, Agent, or Firm—James P. Barr

[57] ABSTRACT

The present invention is directed to a novel method for analyzing aqueous systems to simultaneously quantify the concentrations of multiple active or inactive treating components which may be contained therein. The method comprises determining the absorbance or emission spectrum of the components in the aqueous system over the wavelength range of from 200 to 2500 nm, and then applying chemometrics algorithms to extract and analyze features in the spectrum that are specific to the qualitative and quantitative concentrations from the specific components to simultaneously determine the concentrations of the components.

18 Claims, No Drawings

SPECTROPHOTOMETRIC MONITORING OF MULTIPLE WATER TREATMENT PERFORMANCE INDICATORS USING CHEMOMETRICS

FIELD OF THE INVENTION

The present invention is directed to a method for analyzing the concentration of performance indicators in aqueous systems and more particularly to a method for directly, continuously and simultaneously analyzing multiple performance indicators in aqueous systems which permits optimum control of product active components in the systems.

BACKGROUND OF THE INVENTION

Operation and control of water treatment chemical programs in industrial, municipal, or utility systems typically requires the monitoring of both physical and chemical performance indicators which are important to maintain process system protection. The physical and chemical performance indicators monitored typically include pH, specific anions and cations, inorganic and organic scale inhibitors, corrosion inhibitors, dispersants, and synthetic polymers, etc. It is key to the success of any treatment program that a minimum level, and sometimes a maximum level for economic reasons, of treatment chemicals be maintained in the system.

Control analyses of cooling water, boiler water, and wastewater systems, for example, still typically rely on grab samples. These samples are subsequently analyzed by conventional manual techniques with obvious shortcomings in time, economy and human-error possibilities. In fact, for most industrial water treatment processes analyses are historical rather than dynamic in nature.

Many industrial processes require constant surveillance and control especially process water systems. This requires rapid repetitive analysis with subsequent manual control adjustments or continuous automatic analysis with dynamic control adjustments wherein sensors are coupled directly to computer controllers which are capable of metering chemical feedpumps. A recent technique involves the use of metering devices driven by microprocessors which determine system demand (water flow). Another technique involves measuring an inert component which is added to the system in an amount which is proportional to the total product feed. Neither of the above methods provides a direct analysis of the active treating components and both of these methods assume that the concentration of active treating components are present in the system in a constant proportion which often is not the case. Both methods, therefore, require additional active treating component analyses to assure the correct level of inhibitor, etc.

Recently, ultra-violet, visible and near infrared detectors have been used to quantitatively analyze heavy metal contaminants in multi-component systems. Chemical analysis using ultraviolet, visible, near infrared absorption or emission spectra relies upon relative absorption or emission characteristics at many specific wavelengths over the entire ultraviolet and visible range. Absorption or emission in the ultraviolet, visible, and near infrared (UV-vis-NIR) region of the spectrum is a result of the changes in energy levels that occur in the bond structures and valence electrons of atoms when in contact with a source of ultraviolet-visible light.

The important features of absorption or emission spectra are its position and intensity, which yield a signature that can be used to define qualitative and quantitative characteristics. These data are a function of the absorption or emission intensities detected at many equally spaced wavelength intervals across a range of wavelengths. Absorption of light is governed by the Beer-Lambert Law that define the relationship between incident light absorbed by a solution and the molecular concentration of the solution. In simplified form, the Beer-Lambert law may be stated as:

$$A = abc$$

where,
A = The total amount of light absorbed.
a = absorption coefficient defining
b = length of the absorption light absorptivity of the media
c = concentration of the solution Absorption may also be described in terms of a comparison between the intensity of light transmitted through an absorbing substance compared to the light intensity when no absorbing substance is in the light beam:

$$T = (I/I_0) \text{ and,}$$

$$A = \log(1/T) \text{ or,}$$

$$A = -\log(I_0/I) = abc$$

where,
T = transmittance
A = absorbance
I = intensity of absorbed light $I_0$
I = intensity of incident light $I_0$ It is possible to analyze solutions qualitatively and quantitatively based on the pattern of absorption or emission observed for the solution across this wide range of wavelengths. Since the observed absorption or emission is a function of all of the absorbing or emitting components within the solution, multi-component systems or systems having a high degree of background interferences greatly complicates the problem of analysis.

Several recent developments have made the use of ultraviolet-visible absorption or emission spectroscopy a feasible technology in the water treatment field:

fiber optics permit substantial distance between the analyzer and the substance to be analyzed. The remote analyzer can house a light source, detector, and electronic components. Fiber optic cables convey the source light to an optrode, where the light is transmitted through the sample, then collected and returned to the detector through a companion cable. Optrodes may be immersed in a process tank or flow stream, and then removed after the analysis has been performed, or they may be permanently located at the same point for continuous monitoring. These are two types of IN-SITU analysis. Alternatively, a sample line may be connected to a flow-through cell containing the optrode. This in ON-LINE analysis.

array detectors permit a broad wavelength range to be simultaneously detected at discrete intervals. This eliminates the need to create intervals by altering wavelengths at the source or prior to detection. Instead, a broad source can be used and fully detected. An evaluation can be made of wavelengths which contain absorption or emission features relevant for the analysis. Wavelengths and ranges which do not contain information that contribute to the analysis can be ignored, even though the measurement will include information from the entire range.

chemometrics may be the most meaningful advance in technology that makes on-line analysis possible. This technique is more fully explained in S. D. Brown, "Chemometrics", Anal. Chem. 62. 84R-101R (1990) which is incorporated herein by reference in its entirety.

Chemometrics is the application of statistical and pattern recognition techniques to chemical analysis. Quantitative estimates of chemical concentration in reagentless UV-vis-NIR spectroscopy are based on algorithms, the parameters of which are determined in calibration sequences called learning sets. Learning sets consist of a large number of known samples that are used to determine the parameters of the algorithm. The number of samples required depends on the complexity of the matrix and the number of spectroscopic interferences that are present. It also depends on the number of dependent variables used in the algorithm. As a rule of thumb, the number of samples should be at least 10 times the number of dependent variables employed. In the presence of known and unknown interferences, the goal of multiple sample calibration is to minimize out the effects of interferences. The learning set solutions must typify the interferences and their variability that will be experienced in on-line solutions measured by the analyzer.

Sensors that detect information for multiple constituents in a complex chemical matrix must rely upon very capable analysis algorithms (chemometric techniques) in order to extract information for a specific chemical constituent. These chemometric techniques compare unknowns with calibrated standards and data bases, to perform advanced forms of cluster analysis, and to extract features from unknowns that are used as information in statistical and mathematical models.

It is another object of this invention to provide a method for simultaneously analyzing multiple performance indicators in aqueous systems in real time.

It is another object of this invention to provide a method for simultaneously analyzing multiple performance indicators in aqueous systems without the use of derivitizing agents.

It is a feature of this invention that multiple performance indicators may be simultaneously analyzed in aqueous systems without the need to chromatographically separate the individual performance indicators or to separate background interferences.

It is another object of this invention to provide a method for maintaining an effective water treatment program wherein multiple performance indicators are directly and continuously monitored to detect change and provide control input to assure optimum dosage levels for some or all performance indicators in the aqueous system.

In accordance with the present invention, there has been provided a method for simultaneously measuring the concentration of multiple performance indicators in an aqueous system which comprises analyzing the ultra-violet, visible and/or near infrared spectrum of the aqueous system in the wavelength range of 200 to 800 nm and applying chemometrics algorithms to the spectrum to simultaneously determine the concentrations of the performance indicators.

Also provided in accordance with the present invention is a method for simultaneously measuring the concentrations of multiple performance indicators and one or more inert tracers in aqueous systems which comprises analyzing the ultra-violet, visible and/or near infrared spectrum of the aqueous system in the wavelength range of from 200 to 800 nm and applying chemometrics algorithms Chemometric techniques have recently been found to be useful for the analysis of metals in aqueous media such as wastewater or contaminated groundwater where many different metals as well as other chemical constituents can be present, all of which may independently vary in concentration. Overlapping the closely grouped spectra from individual constituents result in a spectral signature for the solution that is a combination of individual elements. An analysis system must be capable not only of automatically detecting certain significant features for identification of the analytes of interest, it must also be capable of rapidly analyzing these features to arrive at qualitative identification of the analytes and quantitative measurements of their concentrations, and must do so in a chemical matrix that may contain many possible interferants in a variable background.

"On-site and On-line Spectroscopic Monitoring of Toxic Metal Ions using Fiber Optic Ultraviolet Absorption Spectroscopy" Schlager et al (1991) discloses the application of chemometrics for the analysis of heavy metals in water. "Environmental Monitoring using Chemometric Techniques with the Coming Generation of Smart Analyzers" Schlager et al (1991), discloses the application of chemometrics to the field of environmental monitoring. These references, which are incorporated herein their entirety, do not disclose simultaneous multiple analyses of performance indicators in aqueous systems.

SUMMARY OF THE INVENTION

It is an object of this invention to provide a method for simultaneously analyzing multiple performance indicators in aqueous systems. to the spectrum to simultaneously determine the concentrations of the performance indicators and the inert tracers.

DETAILED DESCRIPTION

The present invention is directed to a method for simultaneously analyzing the concentration of performance indicators in aqueous systems in the presence of background matrix interferences without the need for costly and time consuming separation or derivitization techniques, and which provides unique control capabilities which heretofore have not been possible with previous mass balance or inert tracer techniques. As used herein, the terminology "performance indicator" refers to active treating components, i.e., scale inhibitors, corrosion inhibitors, lubricants, metal working fluids, pH regulators, dispersants, defoaming agents, sequestrants, biocides, detackifiers, precipitating agents, and the like which have detectable absorbance or emission characteristics in the ultra-violet, visible and/or near infrared spectrum. These are generally in the nature of treatment chemicals which are added to aqueous systems to protect the system, reduce maintenance, increase efficiency and/or to reduce environmental impact. However, in accordance with the present invention, it is also possible to monitor and quantify inert tracers which are often added to aqueous systems in proportional amounts to active treating components and which are more or as easily monitored than the active component itself. In addition, other species in the aqueous system may also be monitored in accordance with this invention, including naturally occurring background interfering species, such as e.g., dissolved metals or other contaminants as well as contaminants derived from leaks or processes. The performance indicators should have absorbance and/or emission characteristics in the range of 200 to 800 nm, preferably in the range 230–800 nm, and most preferably in the range 230 to 346.

The terminology "aqueous system" as used herein refers not only to purely aqueous systems where water is the major component, but also to systems where water is present in amounts less than 50% such as e.g., oil-in-water or water-in-oil emulsions. These include drilling mud, lubricating fluids, antifreeze formulations and the like.

Thus, it has now been discovered that it is possible to directly and continuously detect the absorption or emission spectra for multiple performance indicators and/or one or more inert tracers in aqueous systems using an ultraviolet-visible-NIR-spectrometer. The spectrometer may be used to monitor off-line samples, or in a preferred embodiment is equipped with an in-situ or on-line fiber optic probe. In general, the method of this invention involves withdrawing a sample from an aqueous system and analyzing the spectrum in the range 200 to 800 nm. The aqueous system may be monitored continuously such as through a flow cell, or discrete samples may be taken and subjected to various flow injection techniques.

In a preferred embodiment, the detector is an on-line UV-vis-NIR diode array spectrometer having a wavelength range of from 200 to 800 nm. It is also possible to use fixed wavelength detectors where discrete elements are placed at specific wavelengths which generally correspond to the absorbance or emission maxima for the particular performance indicator including, but not limited to molecular fluorescence, atomic emission, and the like. Charged-coupled device (CCD) analyzers are also preferred for use herein.

It is preferred that the detector have a resolution of at least 10 nm, preferably 2 nm and most preferably 1 nm. For on-line spectral analysis, a flow through optical chamber (optrode) is required. In these systems, light from a Xenon flash lamp is transmitted to the optrode via quartz fiber optic cable. The light is transmitted through the solution and collected in a second fiber optic cable which transmits the light to the spectrometer. In the spectrometer, the light is converted into an analog voltage which is then read by an on board computer where the spectrum of a previously stored deionized water scan is subtracted from the sample spectrum and a "true" spectrum is generated.

Chemometric algorithms are then used to extract and analyze features in the overall absorption or emission spectra that are specific to the qualitative and quantitative contributions from the specific performance indicators. Four basic steps are involved in the analysis and control of performance indicators in aqueous systems.

A. QUANTIFICATION

The quantification of absorption or emission spectra for performance indicators is used to develop learning sets. This process generally involves scanning several samples of known concentrations of performance indicator in a background matrix that is representative of the aqueous system being monitored and preferably involves scanning actual samples taken from the system being monitored. The detected spectral information is labeled with numerical values that assign the known concentration of the performance indicator to the spectrum.

B. PROCESSING

The processing of raw data reduces noise and optimizes the ability of the chemometric techniques to compare known spectra with unknown spectra or to act on specific features for the spectra of a multicomponent solution to permit analysis of individual performance indicators. Processing of spectra is often performed to aid in the analysis of multi-component solutions or to adjust for noise or drift. Typical techniques include the use of first or second derivatives of the absorption or emission spectrum and the use of Fourier or Walsh transformations. If two original spectra were very similar but not identical, examination of their transformed spectra might reveal their differences. Conversely, if the differences were due to the presence of noise or drift, comparison of transformed spectra may reveal the similarities not evident in the raw data.

C. ANALYSIS

The analysis of absorption or emission data identifies individual performance indicators and is used to calculate an estimate of their concentration in the aqueous solution. Once a learning set has been developed for a number of samples of a performance indicator in a solvent at different concentration levels, chemometric techniques can be used to develop a calibration and perform an analysis for an unknown solution. There are several chemometric techniques that can be used:

1. PRINCIPAL COMPONENT ANALYSIS is a powerful transformation technique that converts a set of correlated variables into a compressed smaller set of uncorrelated variables.

The purpose of this transformation is to rotate the coordinate system in a way that results in the alignment of information on a fewer number of axes than in the original arrangement. This results in a compression of the variables by allowing those variables that are highly correlated with one another to be treated as a single entity. After Principal Components Analysis, a small set of uncorrelated variables will represent most of information that was in the original set of variables, but will be far easier to use in subsequent analytical models.

Typically, 2 to 4 principal components account for 85% to 98% of the variance of the variables. The principal components that relate to particular performance indicators will be the parameters for accurate estimations of chemical concentrations.

Principal component analysis is the preferred chemometric algorithm for use in this invention. In a most preferred embodiment of this invention, the rotated principal component analysis is used. In some cases the reduced set of uncorrelated variables are not strongly correlated with the performance indicator of interest. This may be due to the presence of other analytes or matrix effects.

2. REGRESSION ANALYSIS, typically a multiple linear regression since multiple wavelengths are used to characterize each performance indicator and since multiple performance indicators are usually being monitored. The regression defines the values of known concentrations of the performance indicator in terms of the significant variables in the signatures for the performance indicator, then uses this information to define the best fitting plane for the information using least squares techniques to define each boundary of the plane. The measurements of the variables for the unknown is fit to the plane in order to recognize and assign a predicted value to an unknown concentration of the performance indicator. This technique is generally limited to relatively "clean" systems where there is not a significant amount of background matrix interference.

3. DISCRIMINANT ANALYSIS, where absorption or emission variables at significant wavelengths from the calibration set are used to organize the information for known concentrations of the performance indicator into clustered groups, so that linear decision boundaries can be defined to separate the clusters. A performance indicator of unknown concentration can be matched with the closest group based on detection of the significant variables. Typically, the unknown is assigned a characteristic or average value of the group to which it has been matched. This is a very useful technique for quality screening, where the sample is to be sorted into defined categories (acceptable/suspect/unacceptable) based on measured comparisons between the samples and the clusters. However, this technique requires a very large database to obtain statistically significant results.

D. COMPARISON

The comparison of the calculated results from the concentration determination to predefined set points assures optimum dosage levels for all performance indicators in the aqueous systems and if the results are outside the predefined set points, the dosage amounts may be modified accordingly.

In a preferred embodiment of this invention, a multi sample calibration based on a principal component regression approach with first and second derivative options is used. A stepwise regression of the principal components allows for the selection of the most accurate method for each performance indicator based on the highest coefficient of determination ($r^2$) value and/or agreement with chemical referee techniques.

A further calibration step can be performed if the coefficient of determination is still low from the above calibration sequence. This involves the concept of rotated principal components. Such rotation allows for the concentration of all of the relevant information for a particular performance indicator into a single rotated principal component. We have discovered that the use of rotated principal components gives the invention the ability to detect weak UV-vis-NIR species that would normally not be quantifyable using more conventional chemometric techniques.

The simultaneous measurement of multiple performance indicators is necessary to ensure that the correct level of protection is being applied to the aqueous system. In many cases the function of one chemical treating component can be affected by the presence or absence of another treating component. For example, in cooling waters, the loss of corrosion inhibitor can lead to an increase in corrosion rate in the system. The resulting metallic ions released from corrosion can have a significant impact on the effectiveness of scale control chemicals and may actually cause them to precipitate out of the system. Consequently, the loss of one performance indicator component could indirectly lead to loss of other performance indicators if not corrected in time. Moreover, if measurements of the scale inhibitor alone were made, the logical approach would be to increase the feed rate of scale inhibitor to compensate that lost due to precipitation. Such an action could be problematic if the precipitation continued. This would add to the scale volume and the system may not recover. However if simultaneous measurements of both corrosion inhibitor and scale inhibitor are available, the level of corrosion inhibitor could be adjusted back to acceptable levels and then the scale inhibitor concentration adjusted. Only by simultaneously monitoring the level of each performance indicator in the system can this be detected and the appropriate action taken to solve the problem. By having the monitoring device of this invention connected to a logic controlled feed system, the entire process could be automated to maintain optimum levels of corrosion inhibitor and scale inhibitor at all times.

Another inherent advantage of the method of this invention is the ability to measure treatment reserve or residual treatment. Most performance indicators are consumed to some extent in the treatment process. The measurement of inert tracer plus active component in a product allows the continuous measurement of this well established treatment parameter. No current continuous process can accomplish this technique. For example, it is advantageous to maintain at least a minimum level of treatment in the system. In a phosphate/polymer program, polymer can be consumed in the sludge conditioning process. Monitoring polymer only would show an increased demand during feedwater hardness upset conditions indicating the lack of chemical feed. Monitoring an inert tracer component would show correct product feed levels. By combining both measurements and coupling with sufficient computer controller logic, the treatment reserve or residual polymer would be determined. In addition, a key process parameter would be identified which is the fact that a feedwater upset condition was detected allowing corrective action to be taken as in a softener overrun on hardness. The corrective action would be to regenerate the softener. In addition, active component consumption can also be identified and quantified which is a key control concept.

The method of the present invention may similarly be used in combination with other standard monitoring techniques to provide enhanced, comprehensive control of treatment programs in aqueous systems. These monitoring techniques include, but are not limited to monitors or sensors for measuring pH, conductivity, chlorine, selective ions, deposits, total hardness, colorimetry, fouling, oxidation/reduction probes, turbidity, refractive index, mass balance, as well as chromatographic techniques, and the like, and combinations thereof.

Without further elaboration, it is believed that one of ordinary skill in the art using the foregoing detailed description can use the present invention to its fullest extent. The following examples are provided to illustrate the present invention in accordance with the principles of this invention, but are not to be construed as limiting the invention in any way except as indicated in the appended claims. All parts and percentages are by weight unless otherwise indicated.

EXAMPLES

In all of the examples given the following operating parameters, calibration methods and chemical techniques were employed.

OPERATING PARAMETERS

ON-LINE ANALYZER

Wavelength 200–800 nm
Resolution 1–2 nm Internal Operating temperature 40° C.
Solution path length 0.8 cm

Chemometric Techniques

Learning set size (10–70) samples.
Wavelength range for calibration (30 wavelengths in the range 230–346 nm)
Calibration based on principal component regression of absorbance, first derivative or second derivative.
Calibration based on rotated principal component on absorbance spectrum, first derivative or second derivative.

Chemical Referee Techniques

All analytical solutions were prepared to volumetric standards. Referee techniques used included ion chromatography (Molybdate) and HPLC (Tolyltriazole) and standard field test techniques and are referred to in the examples as "actual".

The waters represented by the examples represent a cross section of water chemistries for a range of water treatment situations (0–50 ppm calcium hardness, boiler water and cooling water) (50–1000 ppm calcium hardness, cooling water, process waters, waste water effluent).

Table 1 shows the different types of performance indicators used in cooling water systems.

TABLE 1

| Typical Cooling Water Performance Indicators | | | |
|---|---|---|---|
| Ferrous Metal Corrosion Inhibitors | Non Ferrous Metal Corrosion Inhibitors | Scale Inhibitors | Microbiocides |
| Chromate | TT | SSS polymeric | Biocide A |
| Molybdate | MBT | SSS/MA polymeric | Biocide B |
| Nitrite Phosphate Benzoate | BT | HEDPA | Chlorine Bromine |
| DPS-48 | (zinc complex). lanthanum complex | | |
| Tiron | (Zinc complex), lanthanum complex | | |

| Abbr. | |
|---|---|
| Biocide A | 5-chloro-2 methyl-4-isothiazolin-3-one (8.6%)/2 methyl-4-isothiazolin-3-one |
| Biocide B | Tetrahydro-3,5-dimethyl-2H,1,3,5-thiadiazine-2-thione |
| DPS-48 | N,N-di(2-hydroxy-5-sulphonic acid benzyl) glycine, sodium salt |
| Tiron | Catechol disulphonic acid |
| TT | Tolyltriazole |
| MBT | 2-Mercaptobenzothiazole |
| BT | Benzotriazole |
| SSS | sodium styrene sulphonate |
| MA | maleic anhydride |
| HEDPA | Hydroxy ethylidene 1,1-diphosphonic acid |

Table 2 shows the simultaneous measurement of three performance indicators in an industrial cooling water. The indicators represent a mild steel corrosion inhibitor (Molybdate), a copper corrosion inhibitor (Tolyltriazole) and an organic biocide (tetrahydro,-3,5-dimethyl-2H-1,3,5-thiadiazine-2-thione). Rotated principal components were chosen for each analyte of interest. The water selected had a hardness in the range (50–800 ppm as calcium carbonate)

TABLE 2

Simultaneous Measurement of Three Performance Indicators in Cooling Water

| Sample Number | Molybdate as $Mo^{6+}$ ppm | | Tolyltriazole ppm | | Biocide B ppm | |
|---|---|---|---|---|---|---|
| | Actual | Observed | Actual | Observed | Actual | Observed |
| 1 | 3.78 | 4.20 | 14.4 | 13.06 | 97 | 115.0 |
| 2 | 4.5 | 4.74 | 2.0 | 3.30 | 100 | 91.1 |
| 3 | 1.64 | 1.46 | 10.0 | 11.80 | 91 | 96.8 |
| 4 | 0.84 | 1.04 | 5.20 | 5.80 | 101 | 89.2 |
| 5 | 4.4 | 4.69 | 2.50 | 2.50 | 119 | 120.8 |
| 6 | 1.33 | 1.26 | 0.86 | 1.29 | 71 | 76.8 |
| 7 | 1.71 | 1.34 | 0.95 | 0.82 | 71 | 61.7 |
| 8 | 4.98 | 5.47 | 7.93 | 8.15 | 91 | 88.3 |
| Mean relative error % | | 11.8% | | 21% | | 8.5% |

Table 3 demonstrates the simultaneous measurement of two components in a water matrix. The respective concentrations of a ferrous metal corrosion inhibitor (Molybdate) and a polymeric scale inhibitor (SSS/MAA) copolymer were simultaneously determined using the method of this invention. Rotated principal components of absorbance were selected for a 20 sample learning set. The water had zero calcium hardness.

TABLE 3

Simultaneous Measurement of Two Peformance Indicators in A Water Matrix

| Sample Number | Molybdate as $Mo^{6+}$ ppm | | SSS/MAA (25:75) ppm | |
|---|---|---|---|---|
| | Actual | Observed | Actual | Observed |
| 1 | 1.0 | 1.01 | 3.50 | 3.56 |
| 2 | 2.50 | 2.51 | 2.0 | 2.02 |
| 3 | 4.0 | 4.04 | 5.0 | 4.97 |
| 4 | 3.3 | 3.36 | 1.2 | 1.26 |
| 5 | 5.0 | 5.09 | 4.5 | 4.51 |
| 6 | 1.8 | 1.81 | 6.0 | 5.96 |
| 7 | 5.8 | 5.88 | 2.9 | 2.86 |
| 8 | 0.5 | 0.51 | 2.5 | 2.45 |
| 9 | 4.5 | 4.56 | 0.7 | 0.73 |
| 10 | 2.9 | 2.90 | 4.0 | 4.01 |
| Mean relative error % | | 1.0% | | 1.7% |

Table 4 shows an example of the benefit of using rotated principal components against simple principal components for a weak UV-vis-NIR absorber zinc(N,N-di(2-hydroxy-5-sulphonic acid benzyl) glycine) complex.

TABLE 4

COMPARISON OF THE USE OF PRINCIPAL COMPONENTS AND ROTATED PRINCIPAL COMPONENTS FOR A WEAK UV-VIS-NIR PERFORMANCE INDICATOR IN COOLING WATER. Zinc (N,N-di(hydroxy-5-SULPHONIC ACID BENZYL) GLYCINE) COMPLEX 10 SAMPLE LEARNING SET
AEP = AVERAGE ERROR OF PREDICTION (ppm)

| SAMPLE NUMBER | PRINCIPAL COMPONENT AEP | ROTATED PRINCIPAL COMPONENT AEP |
|---|---|---|
| 1 | 2.21 | 0.078 |
| 2 | 2.42 | 0.086 |
| 3 | 2.62 | 0.226 |
| 4 | 3.16 | 0.366 |
| 5 | 2.29 | 0.046 |
| 6 | 2.26 | 0.322 |
| 7 | 2.30 | 0.664 |
| 8 | 2.47 | 0.260 |

Table 5 demonstrates the on-line determination of nitrite ion in the presence of significant amounts of a strong UV absorber nitrate. This example shows the simultaneous determination of sodium nitrite and a total nitrite/nitrate as $NaNO_2$. These measurements resulted in a value for the nitrate by subtraction of the nitrite from the total nitrite/nitrate. This application had Error in prediction of nitrite of less than 10% even in waters containing high nitrate.

TABLE 5

DETERMINATION OF NITRITE AND NITRATE IN A SIMULTANEOUS ON-LINE MODE

| SAMPLE # | ANALYTICAL VALUES (ppm) | | | MEASURED VALUES (ppm) | | | |
|---|---|---|---|---|---|---|---|
| | $NaNO_2$ | $NaNO_3$ (as $NaNO_2$) | $NO_2/NO_3$ | $NaNO_2$ | % ERR | $NO_2/NO_3$ (as $NaNO_2$) | % ERROR |
| 1 | 0 | 0 | 0 | −7.8 | ERR | −38.0 | ERR |
| 2 | 150 | 0 | 150 | 146.8 | 2.1 | 84.4 | 43.7 |
| 3 | 300 | 0 | 300 | 303.7 | 1.2 | 247.1 | 17.6 |
| 4 | 450 | 0 | 450 | 418.9 | 6.9 | 362.4 | 19.5 |
| 5 | 600 | 0 | 600 | 579.0 | 3.5 | 527.0 | 12.2 |
| 6 | 300 | 100 | 381.2 | 312.0 | 4.0 | 323.2 | 15.2 |
| 7 | 300 | 200 | 462.4 | 303.4 | 1.1 | 415.1 | 10.2 |
| 8 | 300 | 300 | 543.5 | 326.5 | 8.8 | 518.7 | 4.6 |
| 9 | 150 | 300 | 393.5 | 150.6 | 0.4 | 356.6 | 9.4 |
| 10 | 450 | 300 | 693.6 | 437.8 | 2.7 | 630.4 | 9.1 |

Table 6 demonstrates a measurement of a boiler water scale control performance indicator in the presence of various levels of phosphate, a common anion in boiler water. The samples were cooled to room temperature prior to measurement. Prediction errors for the polymer are within 5% of the analytical referee method.

TABLE 6

DETERMINATION OF SSS/MA COPOLYMER IN BOILER WATER AT 25 C. IN PRESENCE OF PHOSPHATE ANION AT PH 11.0.

| SAMPLE # | PHOSPHATE (ppm) | ANALYTICAL VALUES SSS/MA (ppm) | MEASURED VALUES SSS/MA (ppm) |
|---|---|---|---|
| 1 | 18 | 32.0 | 31.4 |
| 2 | 26 | 12 | 11.8 |
| 3 | 32 | 25 | 24.7 |
| 4 | 42 | 9.0 | 9.0 |
| 5 | 50 | 46 | 46.4 |
| 6 | 58 | 29 | 28.3 |
| 7 | 64 | 16 | 15.9 |
| 8 | 72 | 42 | 41.6 |
| 9 | 84 | 21 | 21.1 |
| 10 | 92 | 36 | 35.8 |

We claim:

1. A method for simultaneously measuring the concentration of multiple performance indicators comprising components used in treating an aqueous system comprising directly determining an absorbance or emission spectrum of the aqueous system in a wavelength range of 200 to 2500 nm, and applying chemometrics algorithms to the absorbance or emission spectrum to simultaneously determine the concentrations of the performance indicators.

2. The method according to claim 1 wherein the concentrations of the performance indicators determined by the chemometrics algorithms are compared to predefined ranges for the respective performance indicators, and if any of the concentrations of the performance indicators are outside the predefined ranges, changing the dosage of those performance indicators which are outside this range.

3. The method according to claim 1 wherein the aqueous system is a cooling water system, a boiler water system, a desalinization unit, a wastewater treatment facility, or pulp or paper processing equipment.

4. The method according to claim 1 wherein the spectrum is analyzed with a UV-vis-NIR diode array spectrophotometer in a wavelength range of from 200 nm to 2500 nm.

5. The method according to claim 1 wherein the chemometrics algorithm is based on a rotated principle component analysis of absorbance or emission spectrum.

6. The method according to claim 1 wherein the performance indicators are selected from the group consisting of scale inhibitors, corrosion inhibitors, lubricants, metal working fluids, pH regulators, dispersants, defoaming agents, sequestrants, biocides, detackifiers, precipitating agents.

7. A method for simultaneously measuring the concentration of multiple performance indicators comprising components used in treating an aqueous system comprising directly determining an absorbance or emission spectrum of the aqueous system which contains the performance indicators in a wavelength range of 200 to 2500 nm, and applying chemometrics algorithms to the absorbance or emission spectrum to simultaneously determine the concentrations of the respective performance indicators and wherein the chemometrics algorithm is based on principle component analysis of the absorbance or emission spectrum.

8. The method according to claim 7 wherein the principle component analysis is based on a first derivative of the absorbance or emission spectrum.

9. The method according to claim 7 wherein the principle component analysis is based on a second derivative of the absorbance or emission spectrum.

10. A method for simultaneously measuring the concentrations of multiple performance indicators comprising one or more treating components and at least one inert tracer in aqueous systems comprising directly determining an absorbance or emission spectrum of the aqueous system in a wavelength range of 200 to 2500 nm, and applying chemometrics algorithms to the absorbance or emission spectrum to determine the concentrations of the performance indicators and the at least one inert tracer.

11. The method according to claim 10 wherein the concentrations of the performance indicators determined by the chemometrics algorithms are compared to predefined ranges for the respective performance indicators, and if any of the concentrations of the performance indicators are outside the predefined ranges, changing the dosage of those performance indicators which are outside this range.

12. The method according to claim 10 wherein the aqueous system is a cooling water system, a boiler water system, a desalinization unit, a wastewater treatment facility, or pulp or paper processing equipment.

13. The method according to claim 10 wherein the spectrum is analyzed with a UV-vis-NIR diode array spectrophotometer in a wavelength range of from 200 nm to 800 nm.

14. The method according to claim 10 wherein the chemometrics algorithm is based on a rotated principle component analysis of absorbance or emission spectrum.

15. The method according to claim 10 wherein the performance indicators are selected from the group consisting of scale inhibitors, corrosion inhibitors, lubricants, metal working fluids, pH regulators, dispersants, defoaming agents, sequestrants, biocides, detackifiers, precipitating agents.

16. A method for simultaneously measuring the concentrations of multiple performance indicators comprising one or more treating components and at least one inert tracer in an aqueous system comprising directly determining an absorbance or emission spectrum of the aqueous system in a wavelength range of from 200 to 2500 nm, and applying chemometrics algorithms to the absorbance or emission spectrum to determine the concentrations of the performance indicators and the at least one inert tracer and wherein the chemometrics algorithms is based on principle component analysis of the absorbance or emission spectrum.

17. The method according to claim 16 wherein the principle component analysis is based on a first derivative of the absorbance or emission spectrum.

18. The method according to claim 16 wherein the principle component analysis is based on a second derivative of the absorbance or emission spectrum.

* * * * *